US008258281B2

(12) United States Patent
Vuylsteke et al.

(10) Patent No.: US 8,258,281 B2
(45) Date of Patent: Sep. 4, 2012

(54) SEX-SPECIFIC MARKER FOR SHRIMPS AND PRAWNS

(75) Inventors: Marnik Vuylsteke, Gent (BE); Frank Van Breusegem, Brakel (BE); Jan Staelens, Rumbeke (BE)

(73) Assignees: VIB VZW, Ghent (BE); Universiteit Gent, Ghent (BE); Moana Belgium NV, Ternat (BE)

( * ) Notice: Subject to any disclaimer, the term of this patent is extended or adjusted under 35 U.S.C. 154(b) by 621 days.

(21) Appl. No.: 12/226,627

(22) PCT Filed: Apr. 25, 2007

(86) PCT No.: PCT/EP2007/054041
§ 371 (c)(1),
(2), (4) Date: Aug. 4, 2009

(87) PCT Pub. No.: WO2007/122247
PCT Pub. Date: Nov. 1, 2007

(65) Prior Publication Data
US 2009/0298066 A1     Dec. 3, 2009

(30) Foreign Application Priority Data

Apr. 25, 2006  (EP) .................................... 06113087

(51) Int. Cl.
*C12Q 1/68* (2006.01)
*C12P 19/34* (2006.01)
*C07H 21/02* (2006.01)
*C07H 21/04* (2006.01)

(52) U.S. Cl. ...... 536/24.3; 435/6.1; 435/6.11; 435/6.12; 536/23.1; 536/24.33

(58) Field of Classification Search ........................ None
See application file for complete search history.

(56) References Cited

FOREIGN PATENT DOCUMENTS

WO    WO 2007/122247    11/2007

OTHER PUBLICATIONS

Li et al., Genetic mapping of the Kuruma prawn *Penaeus japonicus* using AFLP markers, Aquaculture, Apr. 2, 2003, pp. 143-156, vol. 219, No. 1-4.
Perez et al., A sex-specific linkage map of the white shrimp *Penaeus (Litopenaeus) vannamei* based on AFLP markers, Aquaculture, Dec. 20, 2004, pp. 105-118, vol. 242, No. 1-4.
Wilson et al., Genetic mapping of the black tiger shrimp *Panaeus monodon* with amplified fragment length polymorphism, Aquaculture, Feb. 11, 2002, pp. 297-309, vol. 204. No. 3-4.
Maneeruttanarungroj et al., Development of polymorphic expressed sequence tag-derived microsatellites for the extension of the genetic linkage map of the black tiger shrimp (*Penaeus monodon*), Animal Genetics, Aug. 2006, pp. 363-368, vol. 37, No. 4.
PCT International Search Report, PCT/EP2007/054041, dated Jul. 2, 2007.

*Primary Examiner* — Young J Kim
(74) *Attorney, Agent, or Firm* — TraskBritt

(57) ABSTRACT

The present invention relates to a sex-specific marker for shrimps and prawns. More specifically, it relates to a sex-specific PCR-based molecular marker, derived from *Penaeus monodon*, that can be used to determine the sex in shrimps and prawns and can be used for any and all requirements for the determination of genetic sex in shrimp and prawn including, but not limited to, sex determination of very young animals, determination of genetic sex on any animals and setting up monosex cultures.

14 Claims, 2 Drawing Sheets

SEQUENCE LISTING

<160> NUMBER OF SEQ ID NOS: 11

<210> SEQ ID NO 1
<211> LENGTH: 20
<212> TYPE: DNA
<213> ORGANISM: Artificial
<220> FEATURE:
<223> OTHER INFORMATION: INDEL-4 primer

<400> SEQUENCE: 1
ggggtcgcga atgtaaaata                                            20

<210> SEQ ID NO 2
<211> LENGTH: 25
<212> TYPE: DNA
<213> ORGANISM: Artificial
<220> FEATURE:
<223> OTHER INFORMATION: INDEL-5 primer

<400> SEQUENCE: 2
ttttcaaatg cataactgtt agctg                                      25

<210> SEQ ID NO 3
<211> LENGTH: 321
<212> TYPE: DNA
<213> ORGANISM: Penaeus monodon
<220> FEATURE:
<221> NAME/KEY: misc_feature
<222> LOCATION: (35)..(35)
<223> OTHER INFORMATION: n is a, c, g, or t

<400> SEQUENCE: 3
gaattcatta ttcgtttagc gtatttcatt agcanaatgt gaacagtcta acagttcata    60
aagatcctat tttcaaatgc ataactgtta gctgatattc ataattcatg ctctaacaaa   120
atggttccca gtattttaca ttcgcgaccc cttctcaaag tgacattccc tcgactcccg   180
gcatcagttt attatatctt tattacacat ttttagccta agagagagaa aaaaacaata   240
ttcagcaata tatgcaagct ttatttacct attgtaatac aatattccgt ggtgacatgg   300
attcttagta tatgcttact c                                            321

<210> SEQ ID NO 4
<211> LENGTH: 285
<212> TYPE: DNA
<213> ORGANISM: Penaeus monodon
<220> FEATURE:
<221> NAME/KEY: misc_feature
<222> LOCATION: (35)..(35)
<223> OTHER INFORMATION: n is a, c, g, or t

<400> SEQUENCE: 4
gaattcatta ttcgtttagc gtatttcatt agcanaatgt gaacagtcta acagttcata    60
agatcctatt ttcaaatgca taactgttag ctgatattca taatccatgc aaagtggttc   120
ccagtatttt acattcgcga ccccttctca aagcgacatt ccctcgactc ccggcatcag   180
tttgttatat ttttattaca catttttaag cctaagagag agaaaaaaac aatattcagc   240
aatatatgca agctttatttt acctaattgt aatacaatat tccat                 285

<210> SEQ ID NO 5
<211> LENGTH: 16
<212> TYPE: DNA
<213> ORGANISM: Artificial
<220> FEATURE:

```
<223> OTHER INFORMATION: EcoRI-specific AFLP primer

<400> SEQUENCE: 5
gactgcgtac caattc                                                        16

<210> SEQ ID NO 6
<211> LENGTH: 14
<212> TYPE: DNA
<213> ORGANISM: Artificial
<220> FEATURE:
<223> OTHER INFORMATION: MseI-specific AFLP primer

<400> SEQUENCE: 6
tgagtcctga gtaa                                                          14

<210> SEQ ID NO 7
<211> LENGTH: 25
<212> TYPE: DNA
<213> ORGANISM: Artificial
<220> FEATURE:
<223> OTHER INFORMATION: ATTGCA-1 primer

<400> SEQUENCE: 7
tctaacagtt cataaagcat cctat                                              25

<210> SEQ ID NO 8
<211> LENGTH: 23
<212> TYPE: DNA
<213> ORGANISM: Artificial
<220> FEATURE:
<223> OTHER INFORMATION: ATTGCA-2 primer

<400> SEQUENCE: 8
ttaagcatat actaagaatc cat                                                23

<210> SEQ ID NO 9
<211> LENGTH: 33
<212> TYPE: DNA
<213> ORGANISM: Artificial
<220> FEATURE:
<223> OTHER INFORMATION: FemaleForward_2 primer

<400> SEQUENCE: 9
gcgggcgtta gctgatattc ataattcatg ctc                                     33

<210> SEQ ID NO 10
<211> LENGTH: 41
<212> TYPE: DNA
<213> ORGANISM: Artificial
<220> FEATURE:
<223> OTHER INFORMATION: MaleForward_2 primer

<400> SEQUENCE: 10
gcgggcaggg cggcgttagc tgatattcat aatccatgca a                            41

<210> SEQ ID NO 11
<211> LENGTH: 22
<212> TYPE: DNA
<213> ORGANISM: Artificial
<220> FEATURE:
<223> OTHER INFORMATION: Reverse_2 primer

<400> SEQUENCE: 11
aaggggtcgc gaatgtaaaa ta                                                 22
```

SEX-SPECIFIC MARKER FOR SHRIMPS AND PRAWNS

CROSS-REFERENCE TO RELATED APPLICATION

This is a national phase entry under 35 U.S.C. §371 of International Patent Application PCT/EP2007/054041, filed Apr. 25, 2007, published in English as International Patent Publication WO 2007/122247 on Nov. 1, 2007, which claims the benefit under 35 U.S.C. §119 of European Patent Application EP06113087.8 filed Apr. 25, 2006.

TECHNICAL FIELD

The present invention relates to a sex-specific marker for shrimps and prawns. More specifically, it relates to a sex-specific PCR-based molecular marker, derived from *Penaeus monodon*, that can be used to determine the sex in shrimps and prawns and can be used for any and all requirements for the determination of genetic sex in shrimp and prawn including, but not limited to, sex determination of very young animals, determination of genetic sex on any animals, and setting up monosex cultures.

BACKGROUND

Shrimp and prawn cultivation and trade is a very important activity all over the world. The main species under cultivation are *Penaeus monodon* (Giant tiger prawn, Jumbo tiger prawn, Jumbo tiger shrimp, Black tiger prawn, Blue tiger prawn, and Grass shrimp, etc.), mainly cultivated in Asia, with an aquaculture production of about 600,000 tons in 2003; and *Penaeus vannamei* (Whiteleg shrimp, white shrimp), mainly cultivated in the Americas and in China and Thailand, with an aquaculture production that is comparable to *P. monodon*. For those species, aquaculture is far more important than capture.

Increasing demands for aquaculture production mean increasing pressure for the development of more efficient production systems. More and more, modern genetics are used to support stock improvement and breeding programs (Hulata, 2001). Genomic research and gene mapping developed fast during recent times. DNA markers have been characterized for use in establishing pedigrees, linkage mapping and identifying Quantitative Trait Loci (QTLs).

As most *Penaeus* sp. are sexually dimorphic (Hansford and Hewitt, 1994), a lot of effort has been made to find a reliable sex marker, which could help in setting up and maintaining monosex cultures. Several groups developed linkage maps, mainly based on the use of AFLP markers (Moore et al., 1999; Wilson et al., 2002). Pérez et al. (2004) published a sex-specific linkage map of the white shrimp *Penaeus vannamei*. However, they did not identify a sex-linked marker or linkage group. Li et al. (2003) disclosed a sex-specific linkage map of *Penaeus japonicus*, with a presumed sex marker on the maternal linkage map. Zhang et al. (2006) published a linkage map of *P. vannamei*, with sex-linked microsatellite markers present on the female map. In the latter two cases, however, the sex-marker association was not challenged among genetically unrelated individuals.

It should be stressed that the relatively low number of sample meioses within designed populations (e.g., half-sib families) leads to relatively long stretches of chromosomes being in Linkage Disequilibrium (LD). Consequently, in such linkage studies, the observed high LD between marker and sex dimorphism results from the nature of the population rather than from the tight physical linkage. Therefore, markers found via linkage analysis to be in LD with the sex often fail to discriminate between the two sexes in a population of unrelated individuals. Indeed, Li et al. (2003) admit that the presumed marker is not necessarily linked to a sex-specific sequence, and no sequence data are disclosed. Moreover, Zhang et al. (2004) were unable to identify sex-specific markers in *Penaeus chiniensis* using the AFLP approach. Likewise, Khamnamtong et al. (2006) could not identify sex-specific markers in *Penaeus monodon*.

DISCLOSURE OF THE INVENTION

Surprisingly, using AFLP technology, we were able to isolate a prawn or shrimp sex-specific sequence, allowing unambiguous sex determination of both males and females. To identify sex-specific markers, a large-scale bulked segregant analysis (BSA) using AFLP technology was performed in *Penaeus monodon*. An initial screening was performed in one experimental mapping population. Candidate sex-specific markers were confirmed in three additional experimental mapping populations and in a large set of unrelated wild-caught adults. Two markers were consistently sex-specific at all of these stages. One of these two AFLP markers was subsequently converted to a PCR-based co-dominant marker.

A first aspect of the invention is a prawn or shrimp sex-specific sequence. "Sex-specific sequence," as used herein, means that the sequence can be used for unambiguous sex discrimination between males and females. Preferably, the sex-specific sequence is limited in length to allow an easy identification of small differences between male and female sequences. More preferably, the sex-specific sequence is not more than 2000 nucleotides in length; even more preferably, not more than 1000 nucleotides; yet even more preferably, not more than 500 nucleotides; and most preferably, not more than 400 nucleotides in length. Most preferably, the sex-specific sequence is comprising SEQ ID NO:3 and/or SEQ ID NO:4, or a functional fragment thereof.

One preferred embodiment is a female-specific sequence consisting of SEQ ID NO:3. Another preferred embodiment is a sequence consisting of SEQ ID NO:4 for which males are homozygous. "A functional fragment," as used herein, is a fragment carrying a sex-specific single nucleotide polymorphism (SNP) and/or an insertion deletion (INDEL), and/or a fragment that allows amplification of such sex-specific SNP and/or INDEL. As a non-limiting example, the specific fragment comprises a SNP situated at position 106, 121, 161, 191, 198 and/or 291 of SEQ ID NO:3, and/or an INDEL situated at position 62, 111-117, 216 and/or 272 of SEQ ID NO:3. Preferably, the functional fragment is a primer preferably consisting of SEQ ID NO:1 or SEQ ID NO:2. The primer can be used to amplify the sex-specific INDEL situated at position 111-117 of SEQ ID NO:3. Preferably, the prawn or shrimp belongs to the family of the Penaeidae. Even more preferably, the prawn or shrimp is a *Penaeus* sp., including, but not limited to, *P. monodon*, *P. vannamei*, *P. japonicus*, *P. indicus*, *P. merguiensis*, *P. schmitti* and *P. stylirostris*. Most preferably, the prawn or shrimp is *P. monodon*.

Another aspect of the invention is the use of a PCR-based marker to determine the sex in prawns and shrimps. "PCR-based marker," as used herein, can be any nucleic acid sequence that, upon PCR amplification, allows an unambiguous determination of the sex. Preferably, the marker is limited in length to allow an easy identification of small deletions. More preferably, the marker is not more than 2000 nucleotides in length; even more preferably, not more than 1000 nucleotides; yet even more preferably, not more than 500 nucleotides; and most preferably, not more than 400 nucleotides in length. "Nucleic acid sequence," as used herein, may be any nucleic acid sequence including, but not limited to, DNA, cDNA and RNA. The PCR technology used may be any PCR-based technology known to the person skilled in the art. Preferably, the amplified sequence is selected from the group more preferably consisting of SEQ ID NO:3 and SEQ ID NO:4, or a functional fragment thereof, carrying a sex-specific SNP and/or INDEL. Preferably, the marker is amplified using primers selected from the group consisting of SEQ ID NO:1 and SEQ ID NO:2. Preferably, the prawn or shrimp belongs to the family of the Penaeidae. Even more preferably, the prawn or shrimp is a *Penaeus* sp., including, but not limited to, *P. monodon, P. vannamei, P. japonicus, P. indicus, P. merguiensis, P. schmitti* and *P. stylirostris*. Most preferably, the prawn or shrimp is *P. monodon*.

Although the detection of the PCR-based marker is preferably done using a PCR-based technology, it is clear for the person skilled in the art that other technologies, such as, but not limited to, DNA-DNA hybridization, micro-array technology or DNA melting profiles, alone or in combination with PCR amplification, can be used for the detection of the marker sequence.

Still another aspect of the invention is a method of setting up a monosex culture in prawns and shrimps, comprising a PCR-based sex determination according to the invention. The PCR-based sex determination can be used to distinguish between males and females, and select the organisms to be cultured. However, setting up a monosex culture, as used herein, does not imply that the PCR-based sex determination according to the invention should be used in every culture cycle. Indeed, the PCR-based sex determination according to the invention may be used, as a non limiting example, in the selection of homogametic females, which, upon crossing with homogametic males, would give a completely uniform and heterogametic female offspring, resulting in a monosex culture. Preferably, the method comprises the use of primers selected from the group consisting of SEQ ID NO:1 and SEQ ID NO:2. Even more preferably, the sequence, amplified by the PCR-based sex determination is selected from the group consisting of SEQ ID NO:3 and SEQ ID NO:4, or a functional fragment thereof, carrying a sex-specific SNP and/or INDEL. Preferably, the prawn or shrimp belongs to the family of the Penaeidae. Even more preferably, the prawn or shrimp is a *Penaeus* sp., including, but not limited to, *P. monodon, P. vannamei, P. japonicus, P. indicus, P. merguiensis, P. schmitti* and *P. stylirostris*. Most preferably, the prawn or shrimp is *P. monodon*.

DETAILED DESCRIPTION OF THE INVENTION

Examples

Figure 1:
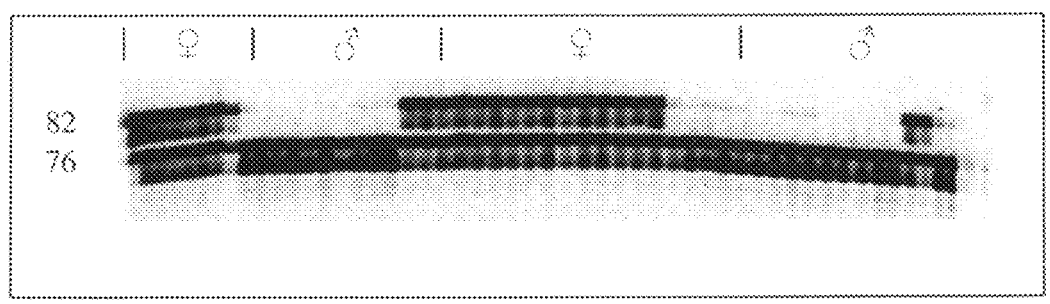
FIG. 1: Genotyping of 52 broodstock animals using the INDEL-marker.

Materials and Methods to the Examples
Animals

Four half-sib mapping populations were generated by crossing two female animals (IC100 and IC67) with two male animals (AL91 and AL99) in all four possible combinations (see Table 1).

TABLE 1

Parents and number of progeny of the four half-sib mapping populations used in this study

| Population | female | male | number of progeny | number of females | number of males | Number of doubts* |
|---|---|---|---|---|---|---|
| A | IC100 | AL91 | 111 | 55 | 45 | 11 |
| B | IC67 | AL91 | 113 | 62 | 45 | 6 |
| C | IC100 | AL99 | 120 | 59 | 61 | 0 |
| D | IC67 | AL99 | 120 | 56 | 57 | 7 |

*The phenotypic sex of these individuals could not be unambiguously determined.

All four parents were recently caught in the wild. All crosses were performed at Moana Technologies, Inc. The mapping populations were harvested at post-larval stage (PL) 120, when the sex of each individual could be scored with an acceptable degree of certainty. In addition, a set of 52 unrelated wild-caught animals was available at Moana Technologies, Inc. These individuals were used to assess the tightness of the physical linkage between the sex-locus and the potential sex-markers identified in the mapping populations.

AFLP Screening

DNA was prepared from snap-frozen pleopod tissue using a CTAB method optimized for shrimp tissue. AFLP analysis was performed as described by Vos et al. (Vos et al. 1995). Genomic DNA of the parents and progeny was restricted using EcoRI and MseI. Double-stranded adaptors were ligated to the ends of the restriction fragments. The digestion product was diluted and pre-amplified using adaptor-specific primers with a single selective nucleotide on each primer. Two pools, or bulks, of five individuals of population A were made at the pre-amplification level. Within each pool, or bulk, the individuals were identical for sex but arbitrary for all other loci. Selected subsets of restriction fragments were amplified using AFLP-primers containing two additional selective nucleotides. Amplification reactions were separated on AFLP sequencing gels and visualized using LI-COR IR$^2$ technology.

AFLP markers identified as sex-specific in the Bulk Segregant Analysis (BSA) on population A (i.e., that were present in the two female bulks but not in the two male bulks) were considered candidate sex-specific markers. Subsequently, these candidate sex-specific markers were tested on the bulked samples from the three remaining mapping populations. Markers that confirmed their association to sex in the three additional BSA analyses were then tested for linkage to the sex-locus in each of the four mapping populations.

To finally assess the strength of the identified marker-trait-associations by linkage, we genotyped the set of 52 unrelated wild-caught (broodstock) animals (the four parents from the mapping populations and 48 additional samples) with the AFLP markers found to be in linkage with sex.

Sequencing

To obtain sequence information from AFLP markers, the EcoRI-specific primer was radioactively labeled using $^{33}$P-ATP and amplification products were separated on a 5% denaturing sequencing gel. Gels were dried and visualized by autoradiography. After visualization, the bands were excised from the gel, and eluted fragments were amplified and sequenced.

PCR Amplification

Most PCR reactions were performed in 1×PCR buffer supplemented with 1.5 ng/μl of each primer, 0.2 mM of each dNTP, 2.5 mM of MgCl2, 0.025 U of Taq polymerase and 100 ng of template DNA.

PCR using primers ATTGCA-1 and ATTGCA-2 were performed in a total volume of 20 µl using 100 ng of genomic DNA as a template. The reaction mixture was heated to 95° C. for four minutes, followed by 35 cycles of 30 seconds of denaturation at 95° C., 30 seconds of annealing at 52° C. and 30 seconds of elongation at 72° C. Finally, an additional elongation step of two minutes at 72° C. was performed.

PCRs using primer ATTGCA-1 in combination with primers MseI+GCA or MseI+AAA and PCR using primer ATTGCA-2 in combination with primer EcoRI+ATT were performed in a total volume of 50 µl using 5 µl of a 1/20 diluted pre-amplification reaction. PCR reactions were as follows: 35 cycles of 30 seconds of denaturation at 95° C., 30 seconds at the appropriate annealing temperature (55° C. for ATTGCA-1 and 53° C. for ATTGCA-2) and 30 seconds of elongation at 72° C. followed by an additional elongation step of two minutes at 72° C.

PCR for the INDEL-marker were performed using either radioactively or fluorescently labeled primer INDEL-4. The reaction was performed in 1×PCR buffer supplemented with 0.3 ng/µl of each primer, 0.2 mM of each dNTP, 2.5 mM of MgCl2, 0.025 U of Taq polymerase and 50 ng of genomic DNA. The reaction mixture was heated to 95° C. for four minutes, followed by 35 cycles of 30 seconds of denaturation at 95° C., 30 seconds of annealing at 55° C., and 30 seconds of elongation at 72° C. Finally, an additional elongation step of two minutes at 72° C. was performed. For the fluorescent analysis, the reaction was essentially the same as for the radioactive analysis except that 0.03 mM of IRD700-labeled INDEL-4 primer was added and 0.3 mM of INDEL-5 primer. Primer sequences are given in Table 2.

TABLE 2

Primer sequences used in this study

| Primer name | Primer sequence (5'-3') | SEQ ID NO: |
|---|---|---|
| EcoRI-specific AFLP primer | GAC TGC GTA CCA ATT C | 5 |
| MseI-specific AFLP primer | TGA GTC CTG AGT AA | 6 |
| ATTGCA-1 | TCT AAC AGT TCA TAA AGC ATC CTA T | 7 |
| ATTGCA-2 | TTA AGC ATA TAC TAA GAA TCC AT | 8 |
| INDEL-4 | GGG GTC GCG AAT GTA AAA TA | 1 |
| INDEL-5 | TTT TCA AAT GCA TAA CTG TTA GCT G | 2 |

SNP Genotyping

Genomic DNA was prepared from a small sample of tissue (e.g., 5 mm of the tip of a walking leg) by heating for 30 minutes at 95° C. in 75 µl of alkaline lysis buffer (25 mM NaOH, 0.2 mM EDTA pH=12). The samples were cooled on ice and 75 µl of neutralization buffer (40 mM Tris-HCl pH=5) was added. PCR was performed on 5 µl of the 1/20 diluted DNA.

PCR was performed using the "Platinum sybr green qPCR supermix-UDG" kit (Invitrogen) using primers FemaleForward_2, MaleForward_2 and Reverse_2. An initial denaturation step (five minutes at 95° C.) was followed by 40 cycles of 20 seconds at 95° C., 30 seconds at 55° C. and 20 seconds at 72° C. Reactions were subsequently denatured (one minute at 95° C.) and renatured (one minute at 40° C.). Melting curve analysis was performed on an iCycler system (Bio-Rad).

Primer Sequences:
FemaleForward_2: GCGGGCGTTAGCTGATATTCATAATTCATGCTC (SEQ ID NO:9)
MaleForward_2: GCGGGCAGGGCGGCGTTAGCTGATATTCATAATCCATGCAA (SEQ ID NO:10)
Reverse_2: AAGGGGTCGCGAATGTAAAATA (SEQ ID NO:11)

Example 1

Marker Identification

In a first screening, we analyzed approximately 1,408 AFLP primer combinations on the bulked samples from mapping population A. The AFLP EcoRI+3/MseI+3 primer combinations generate 50 to 80 AFLP fragments. Hence, the bulks were fingerprinted with more than 70,400 AFLP fragments. Of these fragments, 13 were identified by the BSA analysis as sex-specific. To confirm this, bulked samples from the other three mapping populations (B, C and D) were fingerprinted for these 13 sex-specific markers. In nine cases, the marker-sex association could be confirmed. All of these markers were present in the female bulks but absent from the male bulks.

To determine how tightly these nine markers were linked to the sex-locus, markers were scored in all offspring from the four mapping populations. The recombination frequency (i.e., the number of females that did not show a band and the number of males that did show a band, expressed as a proportion of the total number of individuals analyzed) is expressed in Table 3.

TABLE 3

Recombination frequency between the sex-locus and each of the nine sex-linked AFLP markers in each of the four mapping populations

| MARKER (*) | POPA IC100xAL91 | POPB IC67xAL91 | POPC IC100xAL99 | POPD IC67xAL99 |
|---|---|---|---|---|
| E + AAG/M + CGC-72.8 | 0/100 | 0/96 | 0/120 | 0/109 |
| E + ACC/M + GGG-183.8 | 0/99 | 0/89 | 0/115 | 0/111 |
| E + AAC/M + TAG-200.7 | 1/99 | 6/94 | 2/118 | 4/110 |
| E + AGA/M + CAG-333.0 | 0/99 | 1/92 | 0/117 | 1/108 |
| E + CAG/M + GAG-148.2 | 0/98 | 0/97 | 0/116 | 0/112 |
| E + ACT/M + GTC-284.4 | 0/98 | 0/98 | 0/119 | 0/112 |
| E + AAA/M + GTG-125.4 | 0/98 | 0/91 | 0/119 | 0/112 |
| E + CGG/M + TTG-489.3 | 1/96 | 5/92 | 0/119 | 0/111 |
| E + ATT/M + GCA-347.0 | 0/100 | 0/96 | 0/120 | 0/109 |

(*) E: EcoRI; M: MseI - indicating the sequence of the specific primers according to Table 2, extended with the selective nucleotides applied To assess the degree of LD of the AFLP marker haplotypes with the sexual dimorphism in a population of genetically unrelated individuals, the four parental animals and 48 additional broodstock animals recently caught in the wild at several locations throughout the Pacific Ocean were genotyped at the nine sex-linked AFLP marker loci. At two loci, AFLP marker alleles (EcoRI+AAG/MseI+CGC-72.8 and EcoRI+ATT/MseI+GCA-347.0) were in complete LD with the sex of *P. monodon*.

Example 2

Marker Sequencing

The corresponding EcoRI-specific primers were radioactively labeled. The AFLP amplification products were separated on a denaturing polyacrylamide sequencing gel and visualized using autoradiography. The female EcoRI+AAG/ MseI+CGC-72.8 and EcoRI+ATT/MseI+GCA-347.0 marker alleles were cut from the AFLP gel, eluted, amplified and sequenced. Because we obtained multiple possible sequences, we increased the selectivity of the AFLP reaction by two additional selective nucleotides (+3/+3 AFLP reaction→+4/+4 AFLP reaction). The female-specific fragments were now obtained as EcoRI+AAGT/MseI+CGCT-72.8 and EcoRI+ATTA/MseI+GCAT-347.0. Isolation and subsequent sequencing of the EcoRI+ATTA/MseI+GCAT-347.0 marker band resulted in a unique sequence. A non-specific band hampered the isolation of the EcoRI+AAGT/MseI+CGCT-72.8 fragment and its subsequent generation of a unique sequence. Furthermore, the sequence was short, making it even more difficult to design a specific PCR for this fragment. Therefore, marker EcoRI+ATTA/MseI+GCAT-347.0 was chosen to further develop into a co-dominant PCR-marker.

Figure 2:
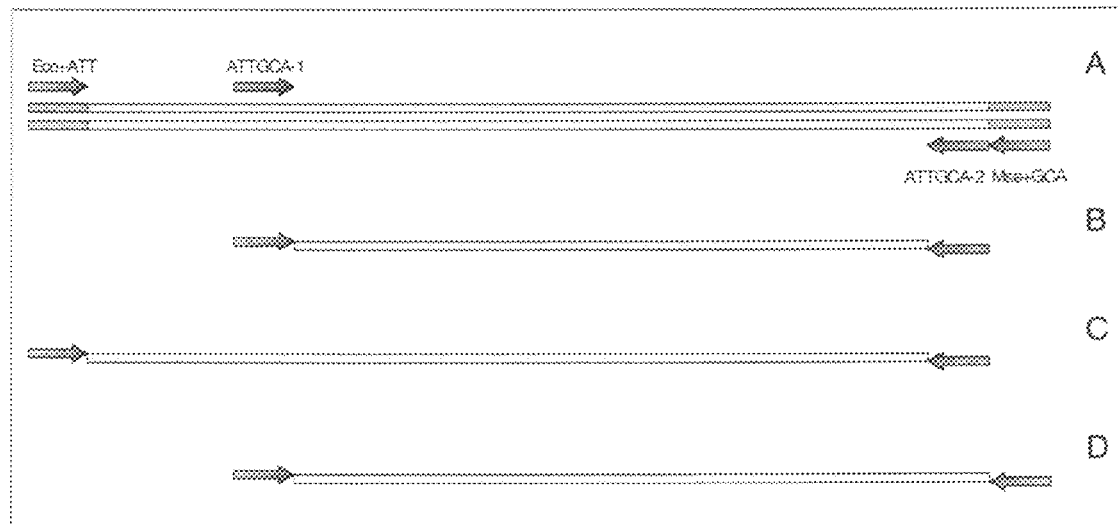
FIG. 2: Schematic representation of the female-specific AFLP fragment (A) and PCR fragments used for obtaining the full sequence of this fragment (B-D).

For marker EcoRI+ATTA/MseI+GCAT-347.0, we designed PCR primers to amplify the marker in both female and male individuals. Using primers ATTGCA-1 and ATTGCA-2, we were able to amplify a fragment of approximately 285 base pairs (bp) on the genomic DNA of both female and male individuals. These PCR fragments were isolated from the gel and sequenced. This resulted in a female- and male-specific sequence for this marker. Careful examination of these sequences revealed nine sex-specific polymorphisms in these sequences: six single nucleotide polymorphisms (SNPs) and three Insertion/Deletion (INDEL) polymorphisms. One of the INDELs caused the presence of an additional MseI restriction site in the male. This is the polymorphism most probably responsible for the absence of the EcoRI+ATTA/MseI+GCAT-347.0 AFLP fragment in the males. To obtain sequence information of the part of flanking regions of the AFLP fragments, we performed PCR using primers ATTGCA-1 and the corresponding MseI-specific AFLP primer (M+GCA for the female and M+AAA for the male) and using primers ATTGCA-2 and the corresponding EcoRI-specific AFLP primer (EcoRI+ATT for both female and male) (see FIG. 2). The resulting PCR fragments were sequenced and the previously obtained sequences were updated using this additional sequence information (SEQ ID NOS:3 and 4). As a result, an additional sequence polymorphism (INDEL) between the male and female sequence was detected, which was previously not identified because it is located in the sequence targeted by primer ATTGCA-1.

Example 3

Conversion of AFLP Marker
E+ATTA/M+GCAT-347.0 to a PCR-Based
Co-Dominant INDEL Marker To convert the E+ATTA/M+GCAT-347.0 AFLP marker into a simple single locus marker, we designed primers to specifically amplify the genomic locus harboring the INDEL polymorphism identified to be sex-specific. Using primers INDEL-4 and INDEL-5, an allelic fragment of 76 bp was amplified in five males and five females coming from population A, and an allelic fragment of 82 bp was amplified in the five females only. This proved that females are the heterogametic sex in Penaeus monodon. A similar result was obtained for the set of 52 unrelated broodstock animals, showing that the INDEL polymorphism is in complete LD with the sex (see FIG. 1). Another set of 33 unrelated broodstock animals was genotyped with this marker and again the INDEL polymorphism was found to be in complete LD with the sex.

The PCR-amplified marker alleles described here are in complete LD with the sex dimorphism in Penaeus monodon. This marker allows the determination of the genetic sex of any P. monodon individual regardless of its developmental stage.

Example 4

Development of an RT-PCR-Based SNP Genotyping
Assay for Sex in P. Monodon

Figure 3:
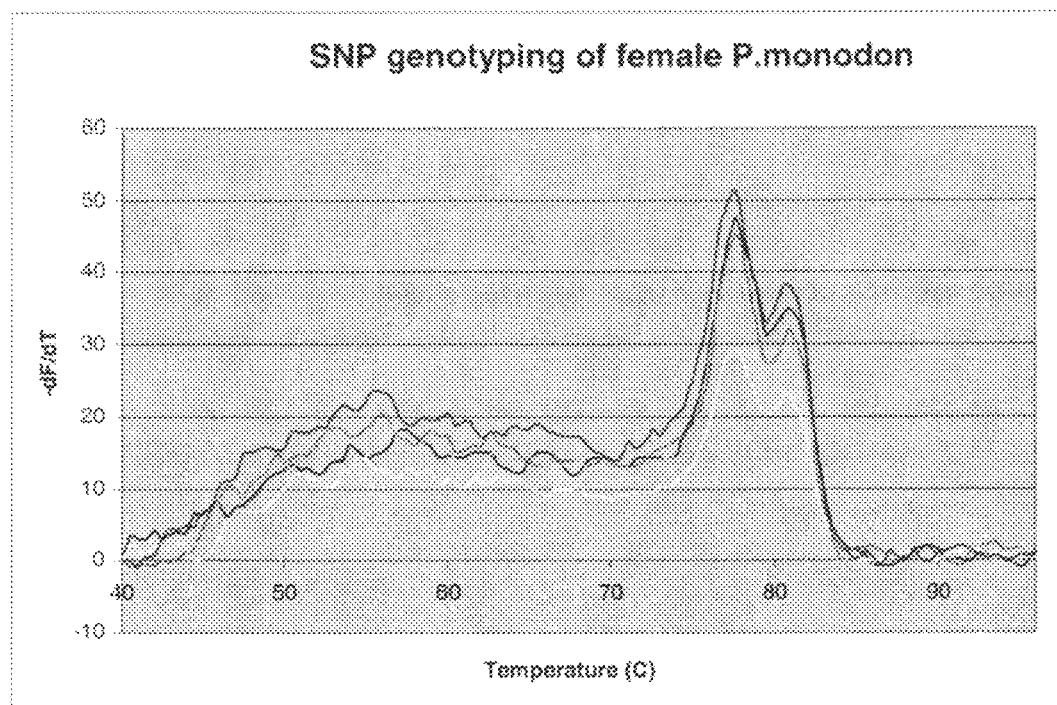
FIG. 3: Melting curves for RT-PCR amplified SNP for female and male *P. monodon*.
Figure 3:
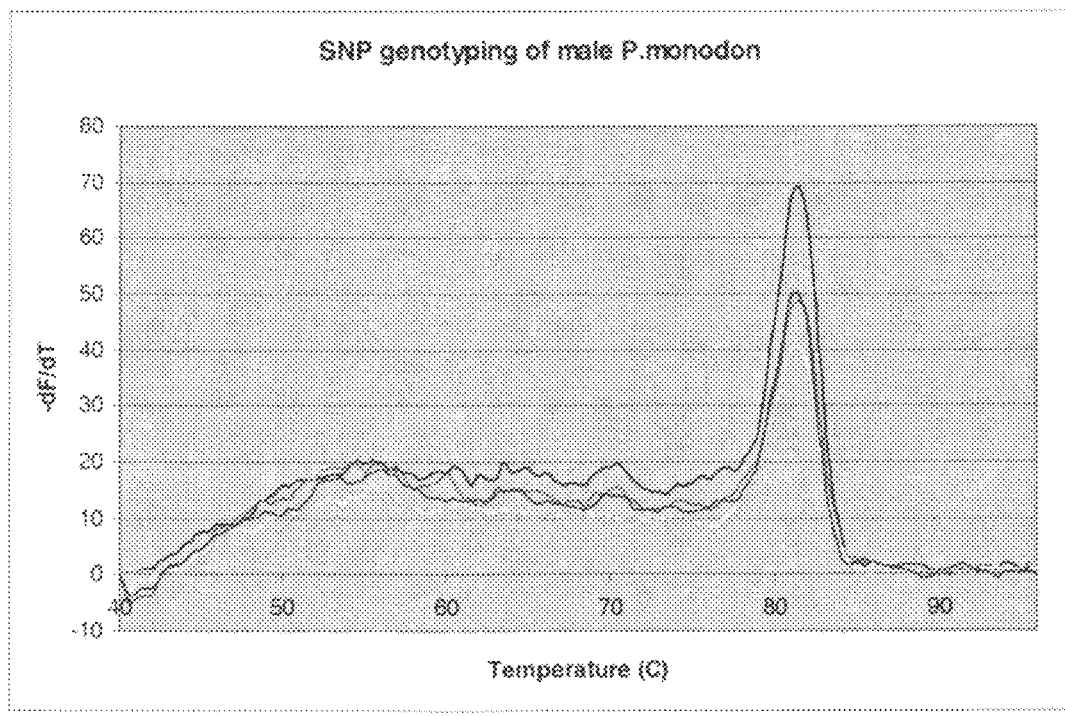

To facilitate the screening of large numbers of shrimp, we developed an RT-PCR-based SNP genotyping assay for the sex marker. Specific forward primers were designed for the male and the female allele and used in a PCR in combination with a common reverse primer. After amplification, melting curve analysis was performed. In males, only one peak was observed, while in the female, two peaks corresponding to the two alleles were observed (FIG. 3).

REFERENCES

Hansford S. W. and D. R. Hewitt (1994). Growth and nutrient digestibility by male and female Penaus monodon: evidence of sexual dimorphism. Aquaculture 125, 147-154.
Hulata G. (2001). Genetic manipulations in aquaculture: a review of stock improvement by classical and modern technologies. Genetica 111, 155-173.
Khamnamtong B., S. Thumrungtanakit, S. Klibunga, T. Aoki, I. Hirono and P. Menasveta (2006). Identification of Sexspecific expression markers in the giant tiger shrimp (Penaeus monodon). Journal of Biochemistry and Molecular Biology 39:1, 37-45.
Li Y., K. Byrne, E. Miggiano, V. Whan, S. Moore, S. Keys, P. Croos, N. Preston and S. Lehnert (2003). Genetic mapping of the kuruma prawn Penaeus japonicus using AFLP markers. Aquaculture 219, 143-156.
Moore S. S., V. Whan, G. P. Davis, K. Byrne, D. J. S. Hetzel and N. Preston (1999). The development and application of genetic markers for the Kuruma prawn Penaeus japonicus. Aquaculture 173, 19-32.
Pérez F., C. Erazo, M. Zhinaula, F. Volckaert and J. Calderon (2004). A sex-specific linkage map of the white shrimp Penaeus (Litopenaeus) vannamei based on AFLP markers. Aquaculture 242, 105-118.
Vos P., R. Hogers, M. Bleeker, M. Reijans, T. van de Lee, M. Homes, A. Frijters, J. Pot, J. Peleman, M. Kuiper, and M. Zabeau (1995). AFLP: a new technique for DNA fingerprinting. Nucl. Acids Res. 23, 4407-4414.
Wilson K., Y. Li, V. Whan, S. Lehnert, K. Burne, S. Moore, S. Pongsomboon, A. Tassanakajon,
G. Rosenberg, E. Ballment, Z. Fayazi, J. Swan, M. Kenway, and J. Benzie (2002).
Genetic mapping of the black tiger shrimp Penaeus monodon with amplified fragment length polymorphism. Aquaculture 204, 297-309.
Zhang L., X. Kong, Z. Yu, J. Kong, and L. Chen (2004). A survey of genetic changes and search for sex-specific markers by AFLP and SAMPL in a breeding program of Chinese shrimp (Penaeus chiniensis). J. Shellfish Res. 23, 897-901.
Zhang L., C. Yang, Y. Zhang, L. Li, X. Zhang, Q. Zhang and Z. J. Xiang (2006). A genetic linkage map of Pacific white shrimp (Litopenaeus vannamei): sex-linked microsatellite markers and high recombination rates. Genetica [ePub ahead of print].

The invention claimed is:

1. A prawn or shrimp sex-specific polynucleotide, comprising SEQ ID NO:3 or SEQ ID NO:4, wherein said prawn or shrimp sex-specific polynucleotide is isolated.

2. The prawn or shrimp sex-specific polynucleotide of claim 1, wherein the prawn or shrimp belongs to the family of Penaeidae.

3. An isolated polynucleotide comprising SEQ ID NO:1 and/or SEQ ID NO:2.

4. An isolated molecular marker comprising the molecule of:
SEQ ID NO:1,
SEQ ID NO:2, or
SEQ ID NO:1 and SEQ ID NO:2.

5. A method of determining a prawn or shrimp's sex, the method comprising:
isolating DNA from the prawn or shrimp;
amplifying a sex-specific polynucleotide in the isolated DNA with a molecular marker of claim 4 as a primer; and
determining the sex in prawn and shrimp.

6. The method according to claim 5, wherein the prawn or shrimp is a *Penaeus* sp.

7. The method according to claim 6, wherein the prawn or shrimp is *Penaeus monodon*.

8. A method of setting up a monosex culture in prawns or shrimps, the method comprising:
determining the sex of a prawn or shrimp by the method of claim 5; and
selecting organisms to be cultured based upon said determination.

9. The method according to claim 8, wherein said prawn or shrimp is a *Penaeus* sp.

10. The method according to claim 9, wherein said prawn or shrimp is *Penaeus monodon*.

11. A method of determining a prawn or shrimp's sex, the method comprising:
isolating DNA from the prawn or shrimp;
amplifying the isolated DNA;
analyzing the amplified DNA for the presence of a sex-specific polynucleotide selected from the group consisting of SEQ ID NO:3, and SEQ ID NO:4; and
determining the sex in prawn and shrimp.

12. An isolated molecular marker, comprising SEQ ID NO:3 or SEQ ID NO:4.

13. The isolated molecular marker of claim 12 consisting of SEQ ID NO:3.

14. The isolated molecular marker of claim 12 consisting of SEQ ID NO:4.

* * * * *

UNITED STATES PATENT AND TRADEMARK OFFICE
CERTIFICATE OF CORRECTION

PATENT NO. : 8,258,281 B2  
APPLICATION NO. : 12/226627  
DATED : September 4, 2012  
INVENTOR(S) : Marnik Vuylsteke et al.

It is certified that error appears in the above-identified patent and that said Letters Patent is hereby corrected as shown below:

On the title page:
In ITEM (73) Assignees, LINE 1 of entry: change "Ghent" to --Zwijnaarde--
In ITEM (73) Assignees, LINE 2 of entry: change "Ghent" to --Gent--

In the specification:
COLUMN 3, LINE 6, change "Penaeidae." to --*Penaeidae.*--
COLUMN 3, LINE 38, change "Penaeidae." to --*Penaeidae.*--
COLUMN 5, LINE 25, change "cycles of30" to --cycles of 30--

In the references:
COLUMN 8, LINES 54,55 delete line break after "(2002)." and before "Genetic"

In the claims:
CLAIM 2, COLUMN 13, LINE 7, change "Penaeidae." to --*Penaeidae.*--

Signed and Sealed this
Twenty-fourth Day of December, 2013

Margaret A. Focarino
*Commissioner for Patents of the United States Patent and Trademark Office*